US 6,588,457 B2

(12) United States Patent
Fotland

(10) Patent No.: US 6,588,457 B2
(45) Date of Patent: Jul. 8, 2003

(54) METHOD FOR PACKAGING UNIFORM SMALL DOSES OF FINELY DIVIDED SUBSTANCES

(76) Inventor: Richard A. Fotland, 1 Crab Apple La., Franklin, MA (US) 02038

( * ) Notice: Subject to any disclaimer, the term of this patent is extended or adjusted under 35 U.S.C. 154(b) by 0 days.

(21) Appl. No.: 10/157,074

(22) Filed: May 29, 2002

(65) Prior Publication Data

US 2002/0179176 A1 Dec. 5, 2002

Related U.S. Application Data

(60) Provisional application No. 60/294,474, filed on May 30, 2001.

(51) Int. Cl.[7] ................................................. B65B 1/04
(52) U.S. Cl. ........................... 141/2; 141/67; 141/131; 141/185; 141/242; 53/235; 53/467; 53/473
(58) Field of Search .............................. 141/2, 18, 67, 141/DIG. 1, 83, 102, 129, 131, 185, 184, 183, 237, 242; 53/235, 467, 473

(56) References Cited

U.S. PATENT DOCUMENTS 5,187,921 A * 2/1993 Wilson et al. ................. 53/453
5,222,529 A * 6/1993 Zoltan et al. .................. 141/4
5,669,973 A    9/1997 Pletcher
5,699,649 A   12/1997 Abrams et al.
5,714,007 A    2/1998 Pletcher et al.

* cited by examiner

Primary Examiner—Steven O. Douglas

(57) ABSTRACT

A method that intermittently or continuously introduces a known mass of fine powder into an aerosolization chamber. The dry powder is aerosolized and, in one preferred method, the aerosol powder charged. Charged powder is then electrostatically deposited into or onto unit dose package substrates as these packages are sequentially moved through the deposition region. The packages are arranged in a continuous line either around the circumference of a circular package transport or in a continuous line on the surface of an endless belt. As each package traverses the precipitation region, a small amount of powder is deposited. The number of packages, the package velocity and the aerosol deposition rate are selected so that a large number of passes are required to fill each package to the required dose level. It is this continuous sampling, or time division sampling (TDS), that very uniformly divides the pre-determined quantity of powder uniformly among the many packages.

20 Claims, 3 Drawing Sheets

METHOD FOR PACKAGING UNIFORM SMALL DOSES OF FINELY DIVIDED SUBSTANCES

This invention provides a process for manufacturing uniform small doses of finely divided substances and more particularly, the invention relates to a technique employing time division sampling for the purpose of packaging accurate small doses of fine pharmaceutical powders. This invention was filed as a provisional patent application No. 60/294,474, on May 30, 2001.

BACKGROUND OF THE INVENTION

The therapy of lung disease often relies on inhaled medications. Bronchodilators have are widely employed in the treatment of asthma. Inhaled aerosolized antiviral agents are employed in the treatment of infectious diseases. Although most inhaled medications are given for their local effect, there is much recent interest in aerosol delivery of medications for systemic absorption. Inhaled drugs, in the form of very small dry powder particles, may be rapidly and directly absorbed into the blood stream. Thus, for example, proteins and peptides may be self-administered rather than administered by injection.

The list of drugs currently under investigation for inhalation delivery is quite extensive. Aerosolized insulin for diabetes is anticipated to become a major application of inhalation therapy.

Most large organic molecules, including proteins and peptides, are denatured by stomach acid when ingested. Absorption in the peripheral parts of the respiratory system overcomes this problem. Thus, the physician has means to provide the patient with a technique whereby the patient may self-administer large molecule medicaments without injection. The value of inhalation therapy in administering insulin, for example, is obvious.

Prior to the development of dry powder inhalers, most inhalation therapies employed pressurized chlorofluorocarbon propellants to disperse drugs. Environmental concern relating to CFC destruction of the earth's ozone layer has reduced the utility of this approach.

Dry powder inhalers for pulmonary drug delivery require dose levels that range from 25 micrograms to over 1,000 micrograms. Powder particle mean diameters of between 0.5 and 5.0 microns are required to provide effective deposition within the lung since larger particles tend to deposit in upper airways without any useful absorption to the circulatory system.

It is difficult to provide metered doses within the required tolerances at the 25 to 250 microgram levels. High-speed weighing systems are generally limited to dose sizes of about 5,000 micrograms or greater and thus require the active pharmaceutical be diluted with an excipient, such as lactose powder, in order to increase the total measured mass. This dilution approach is subject to limitations in mixing uniformity and the aspiration of extraneous matter by the patient.

Another approach for low dose packaging involves dispersing the active powder in a medium that is in a liquid state at room temperature. The packaging substrate is then filled or coated and the liquid evaporated leaving the powder residue on the surface of the substrate. This approach has limitations in view of potential chemical reactions between the pharmaceutical medicament and the dispersing solvent. Government agency approvals are often required for the use of this process because of these potential interaction problems.

Yet another approach for low dose packaging involves the electrostatic precipitation of aerosolized medicament onto the surface of the medicament package. Abrams et al, U.S. Pat. No. 5,699,649, describe a system employing an endless belt that is charged, developed with an aerosolized powder, and the powder image then transferred to the package. The direct electrostatic precipitation of aerosolized powder is disclosed in Pletcher, U.S. Pat. No. 5,669,973. Pletcher et al, U.S. Pat. No. 5,714,007, describe an improvement in this electrostatic precipitation apparatus. These electrostatic deposition techniques require complex control equipment to accurately meter the required dosage into each package. The rate of powder deposition is also limited due to particle transit time effects and limitations in the mass density of the aerosol. Difficulties in re-aerosolizing the particles in the user's inhaler, because of the large electrostatic forces on the charged particles may also be significant.

The present invention provides a cost-effective method for filling unit dose packages with accurate masses of fine powder medicament. In addition, the invention provides a simple direct method for packaging very small doses of fine powders at high production rates and with uniform consistency. The invention provides for deposition onto or into a wide variety of package substrates. While employing electrostatic precipitation of an aerosol, the process does not lead to high levels of electrostatic powder cohesion.

SUMMARY OF THE INVENTION

The invention provides a process that intermittently or continuously introduces a pre-weighed mass fine powder into an aerosolization chamber. The dry powder is aerosolized and, in one preferred method, the aerosol powder charged. Charged powder is then electrostatically deposited into or onto unit dose package substrates as these packages are sequentially moved through the deposition region. The packages are arranged in a continuous line either around the circumference of a circular package transport or in a continuous line on the surface of an endless belt. As each package traverses the precipitation region, a small amount of powder is deposited. The number of packages, the package velocity and the aerosol deposition rate are selected so that a large number of passes are required to fill each package to the required dose level. It is this continuous sampling, or time division sampling (TDS), that very uniformly divides the pre-determined quantity of powder uniformly among the many packages.

Alternately, the packages may be filled using gravity settling.

The method of the invention comprises the steps of:
a. introducing a known weight of fine powder into an aerosolization chamber
b. providing a controlled flow rate of gas
c. adding the known weight of powder into the air stream at a controlled rate to form a low density aerosol form a low density aerosol,
d. providing an endless array of powder packages disposed to move sequentially through the deposition zone
e. adjusting process parameters so that a large number of passes are required to fill each package to the desired dose level
f. recycling the powder packages until all of the powder is consumed
g. removing the now filled packages and replacing with unfilled packages

BRIEF DISCRIPTION OF THE DRAWINGS

DETAILED DESCRIPTION

Figure 1:
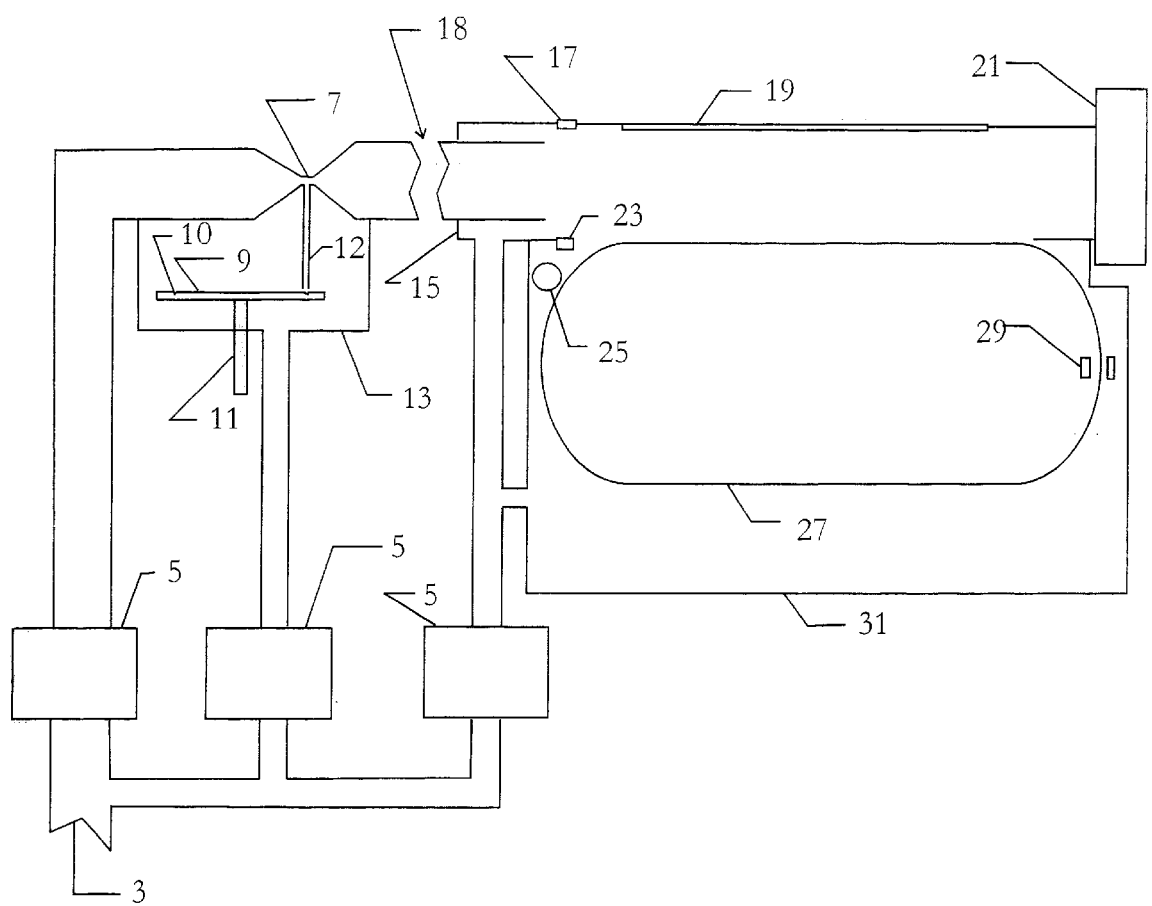
FIG. 1 is a schematic view of a time division sampler filling apparatus employing electrostatic charging of a powder aerosol.

The time division sampler (TDS) shown in FIG. 1 employs an aerosol composed of a dispersion of finely divided powder in a carrier gas. The gas may consist of clean filtered air, with or without humidity control, or consist of a chemically inert gas such as nitrogen, argon, or the like. Inert gases are of value when handling materials such as easily oxidized pharmaceuticals. FIG. 1 shows the use of a controlled atmosphere, which may consist of an inert gas such as nitrogen. In one aspect of the present invention, a filled blister pack may be sealed while maintained in the inert atmosphere, thus providing for drug storage under inert conditions.

Inlet gas is introduced at distribution piping inlet 3. Three flow regulators 5 are employed to control the gas flow rate into each of three manifolds. A major portion of the gas is employed to first aerosolize the material to be deposited and then used to carry this material into the deposition zone. The gas is also distributed to powder loading station 13 to provide an inert atmosphere. The package transport chamber and optional sealing area 31 is also provided with inert gas. Finally, sheath air 15 is provided to isolate the upper and lower surfaces of the deposition chamber from contact with the powder.

One method of introducing powder into the apparatus involves first distributing a known mass of powder into circular powder groove 10 in turntable 9 and then mounting the turntable into the powder table chamber. Turntable 9 is rotated using shaft 11. Aerosolization of the powder is accomplished as the powder is aspirated through tube 12 into a high velocity gas flow in the neck of venture 7. Optional bars, wires, etc may be placed across the aerosol channel immediately after the venturi to introduce high turbulence to assist in breaking up any powder agglomerations. The approximate rate of powder mass flow into the apparatus is determined by the rotational speed of the turntable and the powder loading density in the turntable groove. Since the airflow in the channel is controlled, then the powder mass flow is may be roughly approximated.

A gap 18 is shown in the channel between the venturi and the aerosol charging source. This gap represents an extended channel that provides sufficient length for the conversion of turbulent flow to laminar flow. This length is typically several tens of times the width of the aerosol channel.

The total powder mass is known with a high degree of precision, having been accurately weighted prior to turntable loading. If this known and controlled total powder mass is very uniformly divided among a known number of unit dose packages, then the unit dose is also known and controlled. This invention accomplishes this through the use of an electrostatic filling process that involves time division sampling of the aerosol stream. A known number of unit packages are recycled through the electrostatic deposition zone a rather large number of times. Any nonuniformity in the aerosol mass flow over time is thus integrated out by the sampling process.

The electrostatic precipitator is similar to a conventional two stage precipitators in that the aerosol powder is first electrostaticly charged and then deposited under the influence of an electrostatic field provided by deflection electrode 10. The aerosol charging source comprised of electrodes 17 and 23 may consist of a corona wire or points or it may consist of a silent electric discharge source as described by Pletcher et al, U.S. Pat. No. 5,714,007.

Powder is electrostatically charged as it moves past the charging source and is then deflected to the packages that are moving in the same direction and at approximately the same velocity as the aerosol. The packages are mounted on endless package transport belt 27 that continuously circulates the packages through the deposition region. Deposition of the charged particles results in a net charge being retained in each package. This charge is neutralized using corona discharge source 25. In order to detect system faults, optional sensor 29 may be positioned along the transport path to detect abnormal deposition conditions.

Output air filter 21 consisting of either an electrostatic precipitator or a mechanical unit collects any residual powder, if any, not deposited. This filter may be weighed from time to time to establish the efficacy of the apparatus. This weight may be applied to any correction factor used in calculating final unit dose mass.

Figure 2:
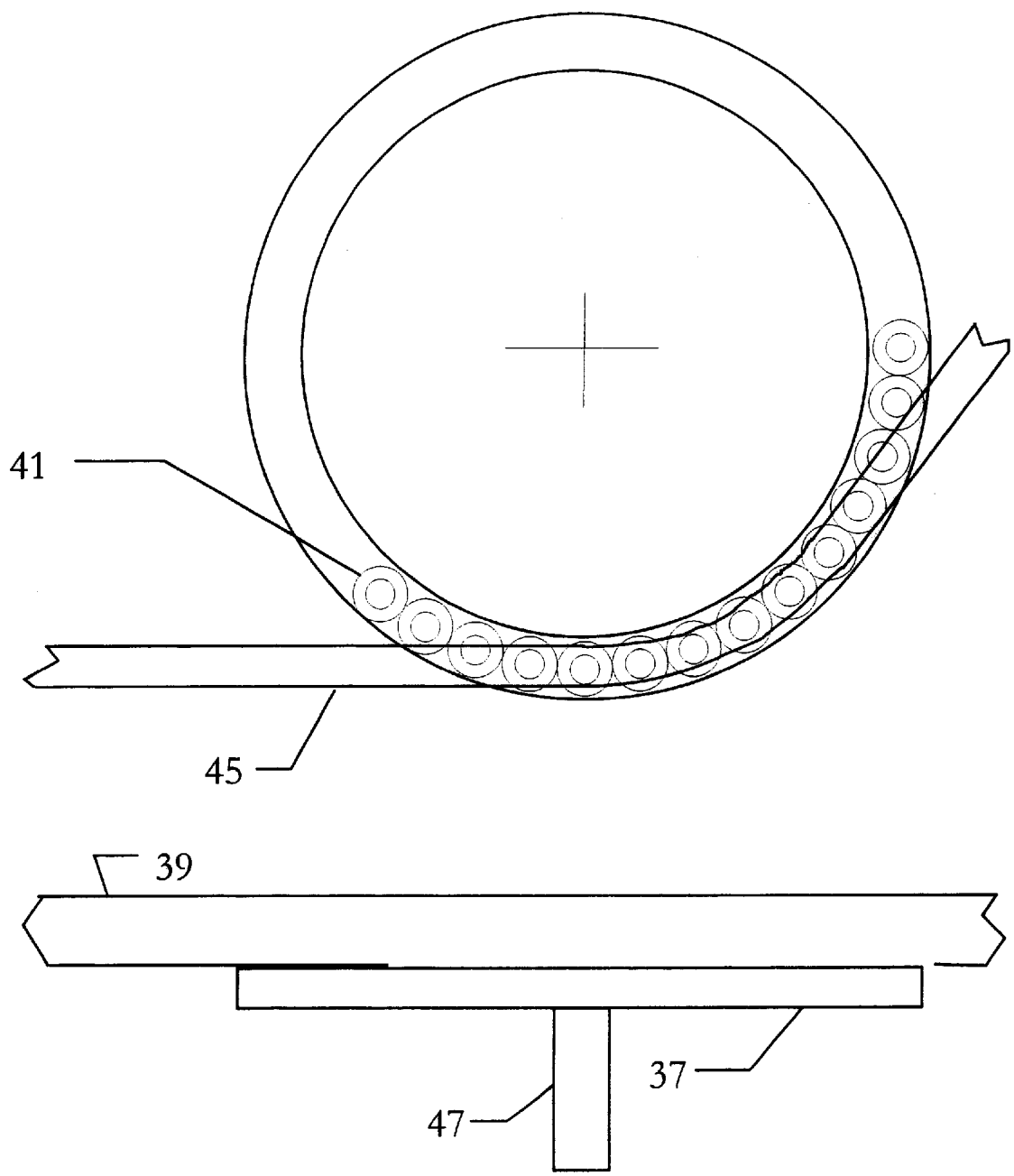
FIG. 2 is a schematic illustration showing an alternate means of cycling packages through a deposition region.

In order to provide uniform sampling, it is required that each package follows the path of all other packages in the endless array. The single line is shown in FIG. 1 as using an endless belt transport. An alternate approach, shown in FIG. 2, employs circular package transport turntable 37. Shaft 47 rotates so that the peripheral speed of turntable 37 approximates the aerosol flow velocity. Here, the packages 41, shown as blister packs, are transported under an aerosol deposition channel that is curved in the deposition region with a radius of curvature matching that of the circular substrate transport. The aerosol flows through plenum, 39 that is enclosed except in regions contiguous to the curved path of the blister packs. In this region, plenum 39 is open at the bottom so that powder may be deposited in the blisters. Charging and deposition electrodes are not shown but are equivalent to those of FIG. 1.

Figure 3:
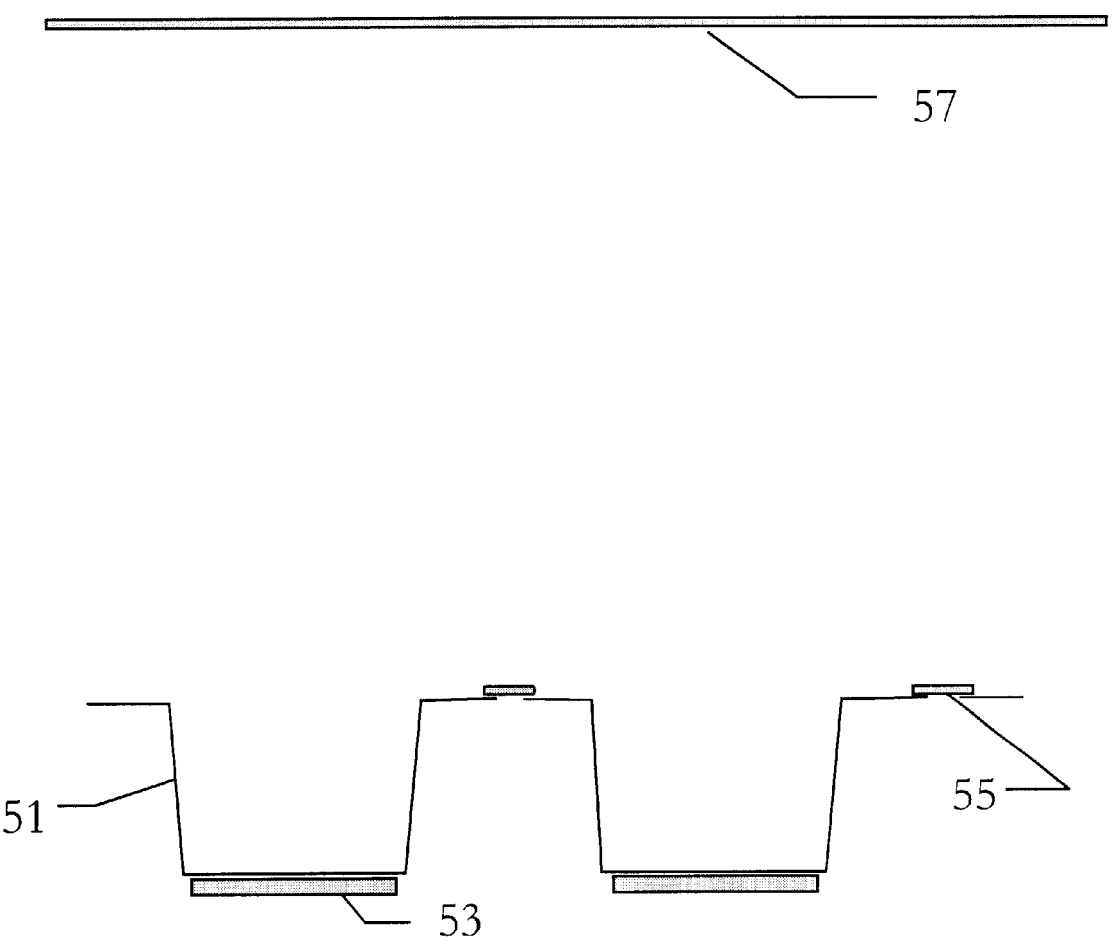
FIG. 3 is a crossection view showing electrostatic deposition electrodes employed to focus powder deposits into blister packs.

FIG. 3 schematically illustrates the field configuration in the deposition zone for the situation in which blister pack cavities 51 are to be filled but no powder is to be deposited external to the cavities. Here, it is required that powder fill the cavities and a negligible amount of powder deposit upon the cavity lip. The use of focusing electrodes 55 concentrates the electric field such that the field lines, and hence the trajectories of charged powder terminate in the blister well (cavity). Precharged aerosol particles are deflected into the blister cavities under the action of the electric field set up by potentials applied between deposition electrodes 57 and 53. Focusing requires that the electric field in the well be higher than the electric field above the well.

While the above description has referenced blister packs, it is understood that the method and apparatus of this invention may apply to other package configurations such as capsules, films, pill boxes, and the like. In addition, although the description refers to an aerosol consisting of a suspension of dry powder, this invention also applies to aerosols of suspended liquid particles.

Alternate methods of aerosol generation may be employed with the TDS apparatus. For example, a spray drying apparatus output may be coupled to the deposition channel so that the spray-dried powder is available in-line with the time division sampler deposition apparatus. A pre-weighted measure of powder may be delivered to the venturi using a vibratory feeder or a screw feeder. Other dry powder aerosol generators are described in "Bioerosols Handbook" edited by Christopher S. Cox and Christopher M. Wathes, Lewis Publishers, N.Y. 1995, p 130–135.

Alternate methods of powder deposition may also be used with the TDS apparatus. These methods include inertial deposition processes such as impingement and dielectrophoretic deposition using a highly divergent electric field.

Gravitational settling may also be employed. In air at standard conditions, the sedimentation velocity of a particle (cm/sec) is equal to $0.0032D^2r$ where D is the particle diameter in microns and r is the particle density in gm/cc. At particle having a diameter of 3 microns and a density of 2 gm/cc will fall at a rate of 0.06 cm/sec. If the settling channel is 0.5 cm high and 300 cm long, then an air velocity of 36 cm/sec will allow the particles to settle. In the case of very long channels, a very large number of packages may be filled for each batch loading. The apparatus may be mounted as a centrifuge to increase the settling rate.

SPECIFIC EXAMPLE 50 milligrams of albuterol, a common bronchodilator employed with dry powder inhalers is loaded into the groove of a 10-cm. diameter powder delivery table. The albuterol has a mean particle diameter of three microns with a range of diameters between 1 and 5 microns. The table groove is milled to a depth of 50 microns and the powder is doctored into the grooves using a doctor knife. The table is mounted in the powder table chamber. This quantity of powder fills about ¾ of the 30 cm circumference of the groove.

One hundred blister cells are mounted on the package transport. These cells are fabricated in a single line and are attached together to facilitate handling. The blister transport is started and accelerated to a velocity of about 100 cm/sec. The blister size and configuration are shown in FIG. 4. The circumference of the endless transport belt is about 90 cm. About 20-cm. of the belt is exposed in the deposition chamber. The belt passing over the drive wheel that, having a radius of about 5 cm, is now revolving at about 180 rpm.

Nitrogen gas is admitted into the venturi at a flow rate of 6 liters/minute and introduced into the chambers to provide a positive nitrogen pressure.

The deposition channel is 1 cm. on a side and the airflow is thus 100 cm/sec. The charging unit is turned on and the deposition field applied. The ac corona wire discharge unit is activated. Air pressure to the air sheath is adjusted to provide a sheath airflow of 100 cm/sec. The rotating table is started and revolves at a rate so that powder is delivered at a rate of 0.5 mg/sec. This corresponds to a table groove velocity near 0.07 cm/sec. At these flow and mass delivery rates, the average aerosol concentration is 5 micrograms/cubic cm. Reynolds number of the channel flow is about 1200 and the flow is thus laminar. One meter of channel is provided between the venturi and the charging source to provide for the transition from turbulent to laminar flow.

Field charging to the powder Pauthenier limit occurs in slightly under 1 millisecond or over a path length of about 1 cm. Mobility of 3 micron particles charged to this limit is about 0.01 $cm^2$/volt-sec. Under the conditions referenced in FIG. 4 (10 kv/cm field), the electrostatic drift velocity is about 100 cm/sec and the furthest particle settles in about a distance of 1 cm. A one-micron particle, however, would require about 3-cm to settle. The 20-cm. provided by the design of this example provides a wide safety factor as well as the opportunity to operate the system at higher flow velocities that the 100 cm/sec of this example.

Another charging configuration employs a corona wire mounted to cross the center of the channel. If the channel width is reduced to 0.5 cm and the wire mounted vertically in the center, then the distance from the corona wire to charging electrodes mounted in each sidewall is only 0.25 cm. Charging then takes place over a very narrow band and few charged particles are expected to deposit upon the surface of the charging electrode. The channel height may also be reduced to 0.5 cm. This will result in a fourfold increase in aerosol velocity. Laminar flow is still preserved and the long path length for electrostatic precipitation assures quantitative deposition.

Simultaneous charging and deposition (single stage electrostatic precipitation) may be realized by employing a series of small corona sources spaced along the deposition path with a pitch equal to the package spacing pitch. The sources are then electrically pulsed as each package passes under each source.

It is inevitable that a small quantity of powder will be lost during each run. Channel wall deposition, uncharged powder depositing on the filter, powder settling on the package lip, etc reduce the total mass available for packaging. As long as this shrinkage is relatively small and relatively constant during successive runs, accurate dose mass will be preserved. Consider the case where between 8 and 12 percent of the powder is not collected in the package. The quantity filled then might vary between 88 and 92 percent; only a 4 percent error.

During deposition, each package is exposed to the deposition region about 100 times. This large number averages out temporal variations in the mass concentration. In similar averaging situations, the noise (variation in dose level) is reduced by a factor of the square root of the number of samples and thus we might anticipate an improvement of a factor of ten in dose to dose variation using the time division sampling of this example.

In the above example, the powder is distributed in a period of about 100 seconds. At this time, the filled blisters and powder supply table are removed and the apparatus is recharged with new blisters and powder. A simple heat sealer and vinyl coated lidding film may be mounted in the package transport chamber and the blister wells sealed in the nitrogen atmosphere prior to being removed from the package transport chamber.

If a complete cycle requires 5 minutes, then about 1200 doses are loaded every hour and about 2 million packages may be filled annually working one shift.

Powders, which do not adhere well to the interior of the blister, may fall out even though the electrostatic discharge does not take place until the package is almost upright. If this is the case, then the optional circular substrate transport of FIG. 2 may be employed. For 100 blisters, the circular table is about 30 cm. in diameter.

The advantages of the process and apparatus of this invention relative to other fine dry powder fill systems include the following:
1. very high unit-dose production rate
2. accurate dose mass due to sampling procedure
3. isolation of the charging and depositing processes minimizes package substrate contamination from charge generator
4. electrostatic forces tending to agglomerate powder in the package are eliminated by the sequential discharge of the deposited powder
5. the process is easily modeled
6. the process is adaptable to a wide range of powders and substrates It is to be understood that variations, modifications, and rearrangements may be made which still come within the scope of the invention.

What is claimed is:

1. A method for packaging uniform small measures of a finely divided substance that comprises the steps of:
   providing a measured quantity of finely divided substance,
   forming an aerosol of said finely divided substance,
   providing a channel for transporting said aerosol, said channel having at least one open side,
   providing a line of packages arranged to move in a closed cycle,
   moving said linear array of packages adjacent to said open side of said channel such that each package passes adjacent said open side channel region a substantial number of times, and
   precipitating said finely divided substance in said packages as they pass adjacent said open side channel region.

2. The method of claim 1 where said finely divided substance is selected from the group of pharmaceutical powders employed in inhalation therapy.

3. The method of claim 1 where said packages comprise blister packs.

4. The method of claim 1 where said finely divided substance consists of liquid droplets.

5. The method of claim 1 where said line of packages are mounted on a turntable that rotates to move said line of packages adjacent said open side channel region.

6. The method of claim 1 where the velocity of said packages moving adjacent said open side of said channel is approximately equal to the velocity of said aerosol moving through said channel.

7. The method of claim 1 where said line of packages are mounted on an endless belt arranged to move adjacent said open side of said channel.

8. The method of claim 1 where said precipitation continues until substantially all of said measured quantity of finely divided substance is precipitated in said packages.

9. The method of claim 1 where said aerosol is formed of said finely divided substance suspended in nitrogen gas.

10. The method of claim 1 where said precipitating occurs by gravitational forces.

11. The method of claim 1 where said precipitating occurs by electrostatic forces.

12. The method of claim 1 where said precipitating is affected by a two stage electrostatic precipitator.

13. A method for packaging uniform small quantities of fine powder that comprises the steps of:
    introducing a known weight of fine powder into an enclosed chamber,
    providing a controlled flow rate of gas,
    dispersing said fine powder into said gas to form an aerosol,
    moving said aerosol through a deposition zone
    providing an endless array of packages disposed to move sequentially through said deposition zone,
    urging said powder to deposit in said packages while traversing said deposition zone,
    adjusting process parameters so that a large number of passes are required to fill said powder packages to the desired dose level,
    recycling said packages until substantially all said known weight of fine powder is deposited in said packages, and
    removing filled packages from said deposition zone.

14. The method of claim 13 where said fine powder deposition occurs through gravitational settling.

15. The method of claim 13 where said fine powder deposition said urging is by means of electrostatic precipitation.

16. The method of claim 13 where said fine powder deposition said urging is provided by electrostatic forces acting upon said powder that has acquired an electrostatic charge.

17. The method of claim 13 where said array of packages are mounted on a turntable that rotates to move said array of packages through said deposition zone.

18. The method of claim 13 where said array of packages are mounted on an endless belt arranged to move through said deposition zone.

19. The method of claim 13 where said packages comprise blister packs.

20. The method of claim 13 where said gas consists of nitrogen.

* * * * *